(12) United States Patent
Yasuda et al.

(10) Patent No.: US 7,300,916 B2
(45) Date of Patent: Nov. 27, 2007

(54) PREVENTIVES/REMEDIES FOR THICKENED SCAR, KELOID OR CHRONIC ARTHRITIC DISEASES

(75) Inventors: Yoshiko Yasuda, 1126-3, Iwakurahataeda-cho, Sakyo-ku, Kyoto-shi, Koyoto (JP); Yukio Nakamura, Higashimurayama (JP); Hitoshi Murakami, Osaka (JP); Koichi Ueda, Takatsuki (JP)

(73) Assignee: Yoshiko Yasuda, Kyoto (JP)

( * ) Notice: Subject to any disclaimer, the term of this patent is extended or adjusted under 35 U.S.C. 154(b) by 290 days.

(21) Appl. No.: 10/469,158

(22) PCT Filed: Feb. 26, 2002

(86) PCT No.: PCT/JP02/01699

§ 371 (c)(1),
(2), (4) Date: Aug. 27, 2003

(87) PCT Pub. No.: WO02/070009

PCT Pub. Date: Sep. 12, 2002

(65) Prior Publication Data

US 2004/0096447 A1    May 20, 2004

(30) Foreign Application Priority Data

Feb. 27, 2001  (JP)  .............................. 2001-052956
Feb. 27, 2001  (JP)  .............................. 2001-052957

(51) Int. Cl.
*A61K 38/00*     (2006.01)
*A61K 39/395*    (2006.01)
*C07K 14/705*    (2006.01)
*C07K 16/26*     (2006.01)

(52) U.S. Cl. .................. 514/2; 424/130.1; 530/388.23

(58) Field of Classification Search ..................... None
See application file for complete search history.

(56) References Cited

U.S. PATENT DOCUMENTS 5,278,065 A * 1/1994 D'Andrea et al. ....... 435/252.3
5,712,370 A * 1/1998 Fibi et al. ............. 530/388.23

FOREIGN PATENT DOCUMENTS

JP    10-101574    4/1998
WO    96/08240     3/1996

OTHER PUBLICATIONS

Yukio et al. Proliferative organ disease treatment and improving agent. English Translation of JP 10-101574 (Apr. 21, 1998).*
Freshney, Culture of Animal Cells, A Manual of Basic Technique, Alan R. Liss, Inc., New York, p. 4 (1983).*
Holmdahl, Dissection of the genetic complexity of arthritis using animal models. Immunology Letters 103:86-91 (2006).*
Kannan et al. Animal models of rheumatoid arthritis and their relevance to human disease. Pathophysiology 12:167-181 (2005).*

* cited by examiner

*Primary Examiner*—Marianne P. Allen
*Assistant Examiner*—Regina M. DeBerry
(74) *Attorney, Agent, or Firm*—Wenderoth, Lind & Ponack, L.L.P.

(57) ABSTRACT

A pharmaceutical preparation for preventing and/or treating hypertrophic scars, keloid or chronic arthritic diseases comprising as an effective component an erythropoietin antagonist. More specifically, there is provided a pharmaceutical preparation for preventing and/or treating hypertrophic scars, keloid or chronic arthritic diseases comprising as an effective component an erythropoietin antagonist such as an anti-erythropoietin antibody, an erythropoietin receptor protein, etc. This pharmaceutical preparation has excellent prophylactic and/or therapeutic effects on collagenous hyperproliferation such as hypertrophic scars, keloid, etc., or chronic arthritic diseases such as rheumatoid arthritis, etc.

4 Claims, 10 Drawing Sheets

PREVENTIVES/REMEDIES FOR THICKENED SCAR, KELOID OR CHRONIC ARTHRITIC DISEASES

TECHNICAL FIELD

The present invention relates to a pharmaceutical preparation for preventing and/or treating hypertrophic scars, keloid or chronic arthritic diseases comprising as an effective component an erythropoietin antagonist. More specifically, the present invention relates to a pharmaceutical preparation for preventing and/or treating hypertrophic scars, keloid or chronic arthritic diseases comprising as an effective component an erythropoietin. antagonist such as an anti-erythropoietin antibody, an erythropoietin receptor protein, etc.

BACKGROUND ART

Hypertrophic scars (keloid) are abnormal proliferation of scar tissue resulting from burns, operative wounds and skin defects after injuries. However, the total number of patients is anticipated to be enormous, and statistics thereof are not available. Although hypertrophic scars resulting from post-operative wounds are of interest to surgery in general, there would be considerable cases wherein hypertrophic scars are left as they are because no effective treatment is available. Therapeutic methods thereof include internal use of tranilast, compression therapy with a sponge, local injection of steroids, and operative treatments such as Z-plasty and dermoplasty. Since therapeutic effects of tranilast and steroids are very mild, only operative treatments may serve as therapies for severe hypertrophic scars. No ointment or injectable preparation suitable for topical administration has been known.

Unlike the above-mentioned hypertrophic scars, keloid (true keloid) is a disease of an unknown cause and is generally said to be influenced by individual's constitutional predispositions. In particular, it is abnormal proliferation of collagen fibers often found in regions such as sternal and shoulder regions, and it develops from both in the presence and absence of a previous injury or an operative wound. Although it is unknown whether the incidence thereof is increasing or not, the number of patients who develop keloid is said to be very large. Therapeutic methods thereof include internal use of tranilast, compression therapy with a sponge, operative treatments, radiation therapies, and the like. However, all these methods have high tendencies of recurrence, and none of them are crucial. No ointment or injectable preparation for this disease is still unknown.

Hypertrophic scars and keloid (sometimes, both are collectively called "keloid") are progressively enlarging scars due to excessive formation of collagen in the dermis and tumor-like swellings. Hypertrophic scars are those developed in the region confined to a primary lesion. Although the cause and pathogenesis of these scars are unknown, accumulation of collagen fibers, complex tangles of collagen fibers, and an increase in the ratio of types III and I collagen (types III/I) have been reported in these scars.

The incidence of rheumatoid arthritis increases with age. Then, the number of cases developing rheumatoid arthritis will increase as the average life span is increased. Since about 0.5% of a population is assumed to be suffering from this disease, about 30 million people out of the world population of 5.9 billion (UN's Demographic Yearbook, 1998) are suspected to be suffering from rheumatoid arthritis. Since the population of Japan is 120 million, there may exist about 0.6 million of patients with rheumatoid arthritis. When atypical types of rheumatoid arthritis are also included, 1 to 1.5% of the population is considered to be suffering from arthrorheumatic diseases, namely there should be about 2 million patients with arthrorheumatic diseases. This number tends to increase year by year due to prolongation of longevity.

Therapeutic methods of rheumatoid arthritis mainly include surgery and medication. As medication, for example, non-steroidal anti-inflammatory drugs, disease modifying anti-rheumatic drugs and steroidal drugs are used. The treatments often start with non-steroidal anti-inflammatory drugs. These drugs can suppress the inflammation, and rapidly relieve the pain, but they cannot prevent the progression of the disease or destruction and deformity of joints. Disease modifying anti-rheumatic drugs can palliate rheumatic disorder by correcting the immune abnormality. There are nine disease modifying anti-rheumatic drugs, which are slow-acting drugs without an analgesic effect and do not respond constantly. Thus, they are not effective for all of the patients. Steroidal drugs have an effect to reduce the symptoms of the inflammation. However, their effect, particularly analgesic effect, is so marked that it is difficult to stop the use of the drug, leading to poor prognosis with short survival due to side-effects of the steroids. Further, these medication are not cause-related therapeutics for rheumatoid arthritis, but they are symptomatic treatment at present.

Rheumatoid arthritis is a chronic arthritic disease characterized by villous proliferation and hypertrophy of synovial membrane, in which, strong infiltration of lymphocytes, monocytes and macrophages with proliferating capillaries are detectable. Further, inflammatory lesions and necrosis are associated in the capillary endothelial cells. These infiltrating cells produce and secrete IL-1, resulting in deterioration and progression of the conditions. Although the causes seen in the lesions are unknown, it is considered that the conditions can be improved if the collagen production associated with the synovial proliferation that is the essential histopathological features is inhibited, and further, IL-1 secreting cells are killed. These treatments are also expected to be effective for diseases with similar joint conditions such as rheumatoid diseases, arthritis with collagenosis, and chronic arthritic diseases such as tendovaginitis, etc.

Erythropoietin (EPO) is involved in proliferation and differentiation of blood cells. Unlike other cytokines, it is not produced in the blood cells, but is produced in kidneys or livers and secreted into blood. Erythropoietin is considered to act on burst forming unit-erythroid (BFU-E) and colony forming unit-erythroid (CFU-E) among erythroid progenitor cells, stimulates them to proliferate and differentiates into erythrocytes (Krantz S. B., Blood, vol. 77, pp. 419-434 (1991)). It is said that, when erythropoietin binds to its cognate receptor on the cell membrane of the progenitor cells, the signal is transduced into the cell nucleus and leads to erythrocyte differentiation, i.e., intracellular accumulation of globin mRNA, hemoglobin production and erythrocyte differentiation (D'Andrea A. D. et al, Cell, vol. 57, pp. 277-285 (1989)). However, the detailed mechanism thereof has not yet been elucidated, and there are many problems to be solved in the future.

In addition to kidney and liver, embryos of the early post-implantation stage (Yasuda Y. et al., Develop. Growth Differ., vol. 35, pp.711-722 (1993)), and brains of humans, monkeys and mice (Marti H. H. et al., Eur. J. Neu. Sci, vol. 8, pp. 666-676 (1996)) have been known to be expression sites of an erythropoietin gene. The present inventors have found that an erythropoietin receptor gene is expressed in mouse decidua in addition to erythroblasts (Yasuda Y. et al., Develop. Growth Differ., vol. 35, pp.711-722 (1993)). Functions of erythropoietin and erythropoietin receptor genes expressed in non-hematopoietic sites are still unknown at present.

Erythropoietin is produced by gene recombinant technique and beneficially used in the treatment of anemia, particularly in anemic patients undergoing kidney dialysis, and in patients in preparation for autologous transfusion during surgery. Erythropoietin receptors are expected to be used as agonists for anemia and antagonists for polycythemia (WO90/08822), and there is described that erythropoietin receptors can be used in the treatment of hypererythropoietinosis and hypererythropoietinemia. Further, there is described that a material which can bind to an erythropoietin receptor at a specific domain may be used in the treatment of chronic rheumatoid arthritis (WO00/66632).

However, while erythropoietin antagonists (erythropoietin-binding substances) such as anti-erythropoietin antibody and erythropoietin receptor protein, are known to have a therapeutic effect on proliferative diseases of the organs such as tumor (JP 10-101574 A), none of their prophylactic and/or therapeutic effects on excessive (unusual) collagenous proliferation such as hypertrophic scars or keloid, and chronic arthritic diseases such as rheumatoid arthritis has been known so far.

OBJECTS OF THE INVENTION

Accordingly, an object of the present invention is to provide a pharmaceutical preparation having excellent prophylactic and/or therapeutic effects on excessive (unusual) collagenous proliferation such as hypertrophic scars or keloid, and chronic arthritic diseases such as rheumatoid arthritis.

SUMMARY OF THE INVENTION

In view of the above object, the present inventors have studied intensively. As a result, it has been found that erythropoietin antagonists such as anti-erythropoietin antibody, etc., have an improving effect on progressive proliferation of collagen fibers, particularly on hypertrophic scars or keloid, as well as on rheumatoid arthritis and the like, thereby completing the present invention.

That is, present invention provides:

(1) A pharmaceutical preparation for preventing and/or treating hypertrophic scars, keloid or chronic arthritic diseases which comprises as an effective component an erythropoietin antagonist (erythropoietin antagonist means a substance having an affinity for erythropoietin);

(2) The pharmaceutical preparation according to the above (1), wherein the erythropoietin antagonist is an anti-erythropoietin antibody;

(3) The pharmaceutical preparation according to the above (1), wherein the erythropoietin antagonist is an erythropoietin receptor protein;

(4) The pharmaceutical preparation according to the above (3), wherein the erythropoietin receptor protein is a soluble erythropoietin receptor protein;

(5) The pharmaceutical preparation according to the above (1), wherein the chronic arthritic disease is selected from the group consisting of rheumatoid arthritis, rheumatoid diseases, arthritis associated with collagenosis, and tendovaginitis;

(6) Use of an erythropoietin antagonist for manufacture of a pharmaceutical preparation for preventing and/or treating hypertrophic scars, keloid or chronic arthritic diseases;

(7) A method for preventing and/or treating hypertrophic scars, keloid or chronic arthritic diseases in mammals which comprises administering an effective amount of an erythropoietin antagonist to the mammals.

BRIEF DESCRIPTION OF DRAWINGS

In FIG. 1, the arrows (←) indicate fibroblasts, arrowheads indicate vascular endothelial cells, and asterisks (*) indicate regions of fibrous bundles (magnification: ×180).

In FIG. 2, the arrows (←) indicate fibrous bundles and smaller arrow indicates a fibroblast (magnification: ×180).

In FIG. 3, the arrows (←) indicate vascular endothelial cells (magnification: ×180).

In FIG. 4, the arrowheads indicate the fragmented collagen bundles, and asterisks (*) indicate the degraded and disappearing collagen bundles (magnification: ×360).

In FIG. 5, the arrow (←) indicates one of collagen bundles (magnification: ×360).

In FIG. 6, the arrows (←) indicate fragments of the nucleus of the endothelial cells (magnification: ×720).

In FIG. 7, the arrows (←) indicate projections of the cytoplasm of the endothelial cells (magnification: ×720).

In FIG. 8, the arrow (←) indicates the calcium deposition to the aggregates of the broken collagen bundles (magnification: ×72).

In FIG. 9, the arrows (←) indicate fibroblasts, and the double arrows (←←) indicate macrophages (magnification: ×150).

In FIG. 10, the arrows (←) indicate monocytes around the pericapillary spaces, the double arrows (←←) indicate macrophages, and arrowhead indicates a fibroblast (magnification: ×600).

In FIG. 11, the arrows (←) indicate fibroblasts (magnification: ×600).

In FIG. 12, the arrows (←) indicate nuclei of fibroblasts, and the double arrows (←←) indicate macrophages (magnification: ×300).

In FIG. 13, the arrows (←) indicate endothelial cells of capillaries with positive reactivity to anti-factor VIII antibody (magnification: ×150).

In FIG. 14, the arrows (←) indicate fibroblasts (magnification: ×600).

In FIG. 15, the arrows (←) indicate fibroblasts, and arrowheads indicate monocytes (magnification: ×480).

In FIG. 16, the arrows (←) indicate fibroblasts, and arrowheads indicate monocytes (magnification: ×480).

In FIG. 17, the arrows (←) indicate the nuclei of dead fibroblasts, and the double arrows (←←) indicate nuclei of dead macrophages (magnification: ×180).

In FIG. 18, the arrows (←) indicate the nuclei of dead fibroblasts, and the arrowheads indicate the vacant foci of collagen fibers located around dead cells (magnification: ×150).

In FIG. 19, the arrows (←) indicate nuclei of fibroblasts, and the double arrows (←←) indicates a bundle of collagen III fibers (magnification: ×300).

In FIG. 20, the arrows (←) indicate nucleus of dead fibroblasts, and the double arrows (←←) indicate fragments of the nucleus (magnification: ×240).

In FIG. 21, the arrows (←) indicate fibroblasts, and the double arrows (←←) indicate macrophages (magnification: ×240).

In FIG. 22, the arrows (←) indicate the damaged blood vessel walls, and the double arrows (←←) indicate pyknotic nuclei of the endothelial cells (magnification: ×360).

In FIG. 23, the arrows (←) indicate vascular endothelial cells, the double arrows (←←) indicate monocytes, and the double arrowheads indicate lymphocytes (magnification: ×360).

In FIG. 24, Lanes 1-5 represent patients with keloid scars, Lane 6 represents atrophic scar and Lanes 7-9 represent red scars.

EPO RT+ denotes that erythropoietin cDNA was amplified in each RNA sample to which reverse transcriptase was added.

EPO RT− denotes that amplification of erythropoietin cDNA was not confirmed in each RNA sample to which reverse transcriptase was not added.

EPOR RT+ denotes that erythropoietin receptor cDNA was amplified in each RNA sample to which reverse transcriptase was added.

EPOR RT− denotes that amplification of erythropoietin receptor cDNA was not confirmed in each RNA sample to which reverse transcriptase was not added.

Beta-actin was used as the internal standard to evaluate the differences in the RNA levels among samples, and amplification thereof is shown with respect to each sample.

Indication above each band distinguishes a particular patient from. others.

Figure 25:
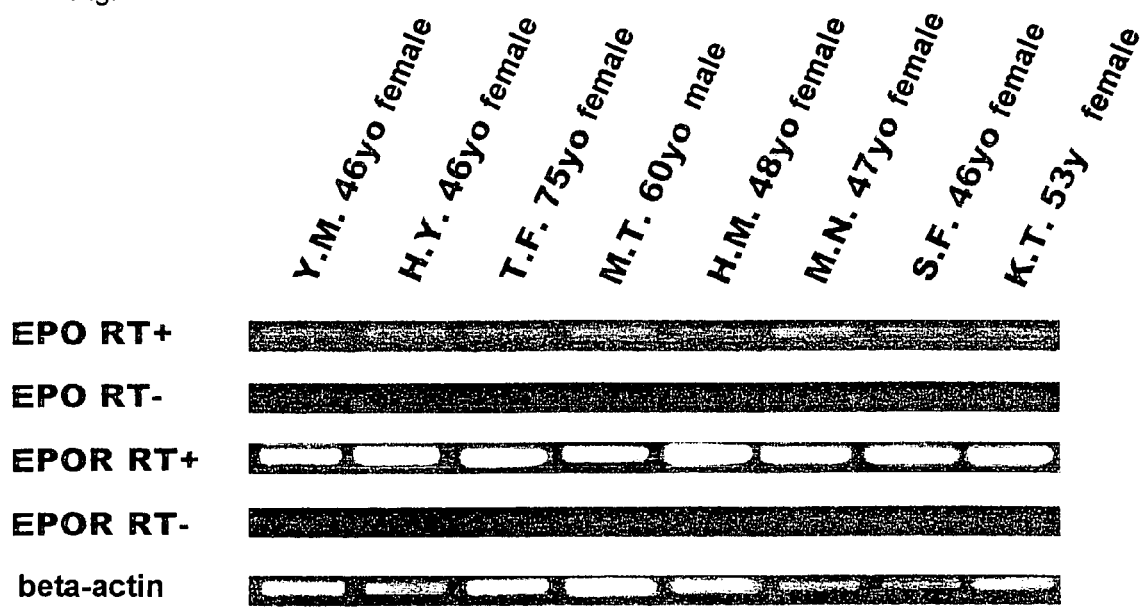

FIG. 25 is a photograph of electrophoresis showing the bands for erythropoietin mRNA and erythropoietin receptor mRNA in synovial tissues. In FIG. 25, EPO RT+ denotes that erythropoietin cDNA was amplified in each RNA sample to which reverse transcriptase was added;

EPO RT− denotes that amplification of erythropoietin cDNA was not confirmed in each RNA sample to which reverse transcriptase was not added;

EPOR RT+ denotes that erythropoietin receptor cDNA was amplified in each RNA sample to which reverse transcriptase was added; and EPOR RT− denotes that amplification of erythropoietin receptor cDNA was not confirmed in each RNA sample to which reverse transcriptase was not added.

Beta-actin was used as the internal standard to evaluate the differences in the RNA levels among samples and amplification thereof in each sample is shown with respect to each sample. Indication above each band distinguishes a particular patient from others.

DETAILED DESCRIPTION OF THE INVENTION

As components, in particular, an effective component of the pharmaceutical preparation for treating hypertrophic scars, keloid or chronic arthritis of the present invention (hereinafter referred to as "the preparation of the present invention"), an erythropoietin antagonist is used. In general, the erythropoietin antagonist of the present invention has an affinity for human erythropoietin similar to that of an antibody for an antigen, or that of a receptor for a ligand, and suppresses autocrine (self secretion) production of erythropoietin. That is, it may be any antagonist of erythropoietin. Examples of the erythropoietin antagonist includes an anti-erythropoietin antibody, an erythropoietin receptor protein, and the like.

The anti-erythropoietin antibody is an antibody that can recognize erythropoietin or its partial peptide, or a salt thereof. The antibody may be either a polyclonal or monoclonal antibody.

The anti-erythropoietin antibody can be produced using erythropoietin or its partial peptide, or a salt thereof as an antigen, in accordance with any known methods for producing antibodies or anti-sera (for example, the method described in JP 01-228492 A).

Salts of erythropoietin or its partial peptide include physiologically acceptable salts with acids (for example, inorganic acids, organic acids, etc.) or bases (for example, alkali metal salts, etc.), among which acid addition salts are preferred. Such salts include, but are not limited to, salts with inorganic acids (for example, hydrochloric acid, phosphoric acid, hydrobromic acid, sulfric acid, etc.), and salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), and the like.

Hereinafter, general methods for preparing the anti-erythropoietin antibody will be illustrated.

[Preparation of Monoclonal Antibody]

(a) Preparation of Monoclonal Antibody Producer Cells

Erythropoietin or its partial peptide, or a salt thereof is administered alone or in combination with a carrier, a diluent and the like to a mammal at a site where the antibody can be produced. Freund's complete adjuvant or Freund's incomplete adjuvant may be administered to enhance the antibody production. Usually, the antigen is administered about 2 to 10 times in total at 2 to 6 weeks intervals. Mammals to be used include, but are not limited to, monkeys, rabbits, dogs, guinea pigs, mice, rats, sheep and goats. Preferably, mice and rats are used.

For preparing monoclonal antibody producer cells, an individual that shows an antibody titer is selected from warm-blooded animals, for example, mice immunized with the antigen, and their spleen or lymph nodes are removed 2 to 5 days after the final immunization. Monoclonal antibody producer hybridoma cells can be prepared by fusion of the antibody producer cells obtained from the spleen or lymph nodes with myeloma cells. The antibody titer in the anti-serum can be determined by measuring the activity of a labeling agent bound to the antibody, for example, after reacting labeled erythropoietin as described hereinafter, etc., with the anti-serum. Fusion can be carried out according to any known method, for example, the method of Kohler and Milstein (Nature, vol. 256, p. 495 (1975)). As a fusion accelerator, there can be used, for example, polyethylene glycols (PEG), Sendai virus, etc., with PEG being preferred.

Examples of myeloma cells include, but are not limited to, P3/NSI/1-Ag4-1, NS-1, P3U1, SP2/0, etc., with P3/NSI/1-Ag4-1 being preferred. The preferred ratio of the number of antibody-producer cells (spleen cells) to the number of myeloma cells is from about 1:1 to 20:1. Cell fusion may be carried out efficiently by adding PEG (preferably, PEG 1000 to PEG 6000) at a concentration of about 10 to 80%, followed by incubation at about 20 to 40° C., preferably at 30 to 37° C. for about 1 to 10 minutes.

For screening monoclonal antibody producer hybridomas, various methods can be used. For example, there are a method in which a culture supernatant of hybridoma cells is added to a solid phase (e.g. microplate) on which an antigen such as erythropoietin is adsorbed directly or in combination with a carrier, and subsequently an anti-immunoglobulin antibody (anti-mouse immunoglobulin antibody is used when mouse cells are used for the cell fusion) labeled with a radioisotope or an enzyme, or protein A is added to the solid phase to detect a monoclonal antibody bound to the solid phase; a method in which a culture supernatant of hybridoma cells are added to a solid phase on which an anti-immunoglobulin antibody or protein A is adsorbed, followed by addition of an antigen such as erythropoietin labeled with a radioisotope or an enzyme to detect a monoclonal antibody bound to the solid phase, and the like.

Selection of monoclonal antibodies can be carried out according to a known method or a modification thereof and, usually, can be carried out in a medium for culturing animal cells supplemented with HAT (hypoxanthine, aminopterin and thymidine), and the like. Any media in which hybridoma cells can grow may be used as a medium for screening and breeding. For example, PRMI1640 medium containing 1 to 20%, preferably 10 to 20% fetal bovine serum, GIT medium containing 1 to 10% fetal bovine serum (WAKO Pure Chemical Industries, Ltd.), or serum-free medium for culturing hybridomas (SFM-101, NISSUI Pharmaceutical Co., Ltd.), etc., can be used. Usually, culture temperature is 20 to 40° C., preferably about 37° C. Culture time is usually 5 days to 3 weeks, preferably 1 to 2 weeks. Usually, culture may be carried out in the atmosphere of 5% $CO_2$. An antibody titer in the supernatant of the hybridoma culture can be determined as described above for determination of the antibody titer in the anti-serum.

(b) Purification of Monoclonal Antibody

Similarly to conventional isolation and purification of a polyclonal antibody, isolation and purification of the monoclonal antibody can be carried out according to a method for isolating and purifying a immunoglobulin [e.g., salting out, alcohol precipitation, isoelectric precipitation, electrophoresis, adsorption and desorption with an ion exchanger (e.g., DEAE), ultracentrifugation, gel filtration, specific purification in which an antigen-bound solid phase or an activated adsorbent such as protein A or protein G is used to collect only an antibody, which is then dissociated the bond].

[Preparation of Polyclonal Antibody]

The polyclonal antibody of the present invention can be produced according to a known method or a modification thereof. For example, the polyclonal antibody can be produced by forming a complex between an immune antigen (an antigen such as erythropoietin, etc.) and a carrier protein, immunizing a mammal according to the above-described method for the production of the monoclonal antibody, collecting a material containing an antibody to erythropoietin, etc., from the immunized animal, and isolating and purifying the antibody.

As for the complex between an immune antigen and a carrier protein used for immunizing a mammal, any kind of carrier protein and any mixing ratio between the carrier protein and a hapten can be used as long as an antibody to the hapten, which is crosslinked with the carrier and used for immunization, is produced efficiently. For example, there can be used a method for coupling bovine serum albumin, bovine thyroglobulin, keyhole limpet hemocyanin or the like with a hapten at a weight ratio of about 0.1 to about 20, preferably about 1 to about 5 of the former: 1 of the hapten.

Various condensation agents may be used for coupling a hapten with a carrier. There can be used glutaraldehyde, carbodiimide, maleimide activated esters, activated ester reagents containing thiol group and dithiopyridyl group, and the like.

The condensation product is administered to a warm-blooded animal alone or in combination with a carrier, a diluent and the like at a site where the antibody can be produced. Freund's complete adjuvant or Freund's incomplete adjuvant may be administered to enhance the antibody production. Usually, the antigen is administered in total about 3 to 10 times at 2 to 6 weeks intervals.

The polyclonal antibody can be obtained from blood, ascites and the like, preferably from blood and the like, of the immunized mammal by using a method as described above.

Determination of the titer of the polyclonal antibody in the anti-serum can be carried out as described above for determination of the antibody titer in the anti-serum. Isolation and purification of the polyclonal antibody can be carried out according to the same isolation and purification of immunoglobulin as that of the above isolation and purification of the monoclonal antibody.

The erythropoietin receptor protein can be obtained using a known method (WO90/08822; JP 06-38787 A; Kagaku to Seibutsu (Chemistry and Biology), 31(4): 270-274; U.S. Pat. No.-5,292,654, etc.). Among erythropoietin receptor proteins, in particular, a soluble erythropoietin receptor protein is preferably used. The soluble erythropoietin receptor protein can be obtained by a known method, for example, that described in JP 06-38787 A, etc. These erythropoietin receptor proteins as well as an anti-erythropoietin antibody bind to erythropoietin in the organ or tissue to block the binding of erytbropoietin to an erythropoietin receptor. Thus, the erythropoietin receptor protein and an anti-erythropoietin antibody are considered to be equivalent substances to each other in the function.

As described above, the erythropoietin receptor protein is a known protein, and its nucleotide and amino acid sequences are disclosed in the above-described patent gazettes or other literatures. In general, the erythropoietin antagonist of the present invention has an affinity for human erythropoietin similar to that of a receptor for a ligand, preferably in a reversible manner, and suppresses autocrine (self secretion) production of erythropoietin. That is, it may be any antagonist of erythropoietin. Then, it may be a human erythropoietin receptor protein or a fragment affinity for erythropoietin, or erythropoietin receptor proteins or their fragments from non-human mammals (for example, mice, etc.) that show at least about 50%, preferably at least about 60%, more preferably at least about 70%, even more preferably at least about 80%, further more preferably at least about 90%, and most preferably at least about 95% homology to a human erythropoietin receptor protein, or analogs thereof.

The preparation of the present invention is safely administered to a human being or animals parenterally (for example, topically, intravenously, transdermally, per rectum, intranasally, transvaginally, through oral mucosa, through lung mucosa, etc.). Dosage forms include injectable preparation, preparation for instillation, suppository, intranasal preparation, sublingual preparation, percutaneous absorption preparation, external preparation, sustained release preparation, powder inhalation, etc. Among these preparations, solid preparations can be prepared according to a known method for preparing a pharmaceutical preparation by using, as a pharmaceutically acceptable carrier, excipients (for example, lactose, sucrose, D-mannitol, starch, corn starch, crystalline cellulose, light anhydrous silicic acid, etc.), stabilizers, coloring agents, surfactants, binding agents (for example, crystalline cellulose, sucrose, D-mannitol, dextrin, hydroxypropylcellulose, hydroxypropylmethylcellulose, polyvinyl pyrrolidone, starch, sucrose, gelatin, methyl cellulose, sodium carboxymethylcellulose, tragacanth gum, gum arabic, etc.), lubricants (magnesium stearate, calcium stearate, tarc, colloidal silica, etc.), other additives and the like to obtain the desired preparation.

For liquid preparations, a mixture of a pharmacologically effective amount of the active component, an erythropoietin antagonist, and an excipient/an activating agent and a solvent (for example, injectable water, alcohol, propylene glycol, macrogol, sesame oil, corn oil, etc.) is prepared. To this mixture may be added other excipients/activating agents (or isotonizing agents) which are generally formulated in injectable preparations such as amino acids (for example, basic amino acids such as arginine, lysine, histidine, ornithine, etc., acidic amino acids such as aspartic acid, glutamic acid etc.), saccharides (for example, glucose, D-sorbitol, D-mannitol, etc.), cellulose derivatives, inorganic salts (for example, sodium chloride, etc.), other organic/inorganic compounds, and the like. When an injectable preparation is prepared by using the active component and these excipients/activating agents, various injectable preparations may be prepared according to a conventional method, if necessary, by adding pH adjusting agents (for example, carbonic acid, phosphoric acid, citric acid, hydrochloric acid, sodium hydroxide, etc.), buffering agents (for example, phosphate, acetate, carbonate, citrate, etc.), stabilizing agents (for example, human serum albumin, polyethylene glycol, polylactic acid, etc.), solubilizing agents (for example, alcohols (e.g. ethanol), polyalcohols (e.g. propylene glycol, polyethylene glycol), non-ionic surfactans (e.g. polysorbate 80™, HCO-50), etc.), soothing agents (for example, benzalkonium chloride, procaine hydrochloride, etc.), preservatives (for example, benzyl alcohol, phenol, etc.), anticoagulants (for example, dextran sulfate, heparin, etc.), antiseptic agents (for example, parahydroxybenzoate esters, chlorobutanol, benzyl alcohol, phenethyl alcohol, dehydroacetic acid, sorbic acid, etc.), antioxidants (for example, sulfite salts, ascorbic acid, etc.), and the like. Injectable solutions thus prepared are usually filled in appropriate ampoules. For administration, the above injectable composition is dissolved in a conventional aqueous diluent and used as an liquid preparation. Examples of the aqueous diluent include glucose solution, physiological saline, Ringer's solution and nutritional supplements, and the like.

The pharmaceutical preparation thus obtained may be administered to human beings and non-human mammals (for example, rats, mice, rabbits, sheep, pigs, cattle, cats, dogs and monkeys), since it is safe and less toxic.

When the injectable preparation contains phosphoric acid or its salt, the concentration of sodium phosphate or potassium phosphate in the injectable preparation may be about 0.1 mM to about 500 mM, preferably about 1 mM to about 100 mM.

For preparing an aseptic preparation, there can be employed an sterile processing including, but being not limited to, an aseptic processing throughout the entire production steps, sterilization by gamma irradiation, addition of antiseptic agents, and the like.

The preparation of the present invention may also be prepared by dissolving a suspension in which the active component is dispersed and formulating in a dosage form such as microcapsules, spherical shape, bar-shape, needleshape, pellets, films, and the like according to a conventional method. Further, the preparation of the present invention may also be formulated into a sustained release preparation comprising the active component and a biodegradable polymer compound. Such a sustained release preparation can be prepared according to the method described in JP 09-263545 A.

In the pharmaceutical preparation of the present invention, the content of the erythropoietin antagonist varies according to a particular dosage form but, usually, the content is about 0.1% to about 100% by weight, preferably about 10% to about 99.9% by weight, more preferably about 20% to about 90% by weight based on the total weight of the preparation.

In the pharmaceutical preparation of the present invention, the content of components other than the erythropoietin antagonist varies according to a particular dosage form but, usually, about 10% to about 99.9% by weight, preferably about 20% to about 90% by weight based on the total weight of the preparation.

When the pharmaceutical preparation of the present invention is used for preventing and/or treating hypertrophic scars and keloid, the preparation of the present invention can be specifically used for preventing, treating and/or ameliorating diseases including postoperative scars, burn keloid, keloid, posttraumatic keloid, restenosis after percutaneous coronary angioplasty, hypertrophic scar pannus, etc. It is particularly preferred that the preparation of the present invention is formulated into an injectable preparation, or into an external preparation such as ointment, and administered directly and topically.

For the external preparation, a solid, semisolid or liquid form may be used. For example, the solid external preparation can be prepared by using the erythropoietin antagonist itself to form a powder composition, or by adding and mixing with additives such as excipients (for example, glycol, mannitol, starch, crystalline cellulose, etc.), thickening agents (for example, natural gums, cellulose derivatives, acrylic polymer, etc.) to form a powder composition. In case of the semisolid external preparation, aqueous or oil-based gels or ointments are preferred. The liquid external preparations may be prepared by almost the same manner as that of the injectable preparation to form an oil or aqueous suspension. To the solid, semisolid or liquid external preparations may be added pH adjusting agents (for example, carbonic acid, phosphoric acid, citric acid, hydrochloric acid, sodium hydroxide, etc.) and antiseptic agents (for example, parahydroxybenzoates, chlorobutanol, benzalkonium chloride, etc.). Specifically, an ointment containing about 0.1 to about 100 mg, preferably about 1 to about 50 mg of the erythropoietin antagonist per 1 g of the ointment is prepared by using vaseline or lanoline as a based and applied to the skin or nasal mucosa.

The dosage varies depending on particular severity of disease, age, weight, dosage form, administration route, dosage regimen, subject animal (mammals, for example, human beings, rats, mice, cats, dogs, rabbits, cattle, pigs, etc.). For example, for an adult person (60 kg of body weight), a single dose of about 0.1 to about 100 mg, preferably about 1 to about 50 mg, more preferably about 2 to about 20 mg of the erythropoietin antagonist may be administered once to three times daily.

When the pharmaceutical preparation of the present invention is that for preventing and/or treating chronic arthritic diseases, the preparation of the present invention may be used to prevent, treat and/or ameliorate any arthritis showing inflammation in the joints, specifically, for example, arthritis from chronic rheumatoid arthritis, rheumatoid diseases, chronic inflammation from collagenosis, tendovaginitis or the like. In particular, the preparation of the present invention is preferably formulated in a liquid preparation such as an injectable preparation and administered directly and topically.

In case of administration to the articular cavity as a topical preparation, such a preparation can be prepared by dispersing the active component using an injectable hyaluronic acid preparation (for example, Kaken Pharmaceutical Co., Ltd.: Arutsu injection) as a dispersion medium. Hyaluronic acid used in the dispersion medium may be a non-toxic salt of hyaluronic acids for example, an alkali metal salt such as sodium, potassium, etc., and an alkaline earth metal salt such as magnesium, calcium, etc. Among them, the sodium salt is preferably used. There can be used hyaluronic acid or a non-toxic salt thereof with a molecular weight of about 200,000 to about 5,000,000 (viscosity method), preferably about 500,000 to about 3,000,000, and more preferably about 700,000 to about 2,500,000.

The final concentration of hyaluronic acid or sodium hyaluronate in the dispersion medium is preferably lower than 1% (w/v) from the viewpoint viscosity suitable for ease of various manipulation, administration, and the like. In particular, the concentration is preferably ranging from about 0.02 to lower than 1%, more preferably ranging from about 0.1 to 1% (w/v).

A pH adjusting agent, a topical anesthetic, an antibiotic, a solubilizing agent, an isotonizing agent, an anti-adsorbent, a glycosaminoglycan, a polysaccharide, etc., may be added to the above-mentioned dispersion medium according to a per se known method. Preferred examples of such additives include mannitol, sorbitol, sodium chloride, glycine, ammonium acetate, a water-soluble protein that shows no substantial pharmacological activity and can be injectable into the body fluid. The glycosaminoglycan includes hyaluronic acid, chondroitin, chondroitin sulfate A, chondroitin sulfate C, dermatan sulfate, heparin, heparan sulfate, keratan sulfate, etc. The polysaccharide includes acidic polysaccharides such as arginic acid, etc.

The water-soluble protein may be any proteins which can be dissolved in water, physiological saline or buffers, and includes, for example, human serum albumin, human immunoglobulin, collagen, gelatin, etc. The pH-adjusting agent includes, for example, glycine, ammonium acetate, citric acid, hydrochloric acid, sodium hydroxide, etc. The above topical anesthetic includes, for example, chlorobutanol, xylocaine hydrochloride, etc. The antibiotic includes, for example, gentamycin, etc. The solubilizing agent include, for example, glycerin, polyethylene glycol 400, etc. The isotonizing agent includes, for example, mannitol, sorbitol, sodium chloride, etc. The anti-adsorbent includes, for example, polyoxyethylene sorbitan monooleate, etc.

Further, when the dispersion medium contains a water-soluble protein, the content of the water-soluble protein may be preferably 0.05 to 50 mg, more preferably 0.5 to 20 mg, further more preferably 0.75 to 10 mg in a single dosage form of the preparation. The preparation may contain phosphoric acid or a salt thereof (for example, sodium phosphate, potassium phosphate, etc.).

When the pharmaceutical preparation of the present invention is that for preventing and/or treating chronic arthritic diseases, the dosage varies depending on particular severity of disease, age, weight, dosage form, administration route, dosage regimen, subject animal (mammals, for example, human beings, rats, mice, cats, dogs, rabbits, cattle, pigs, etc.). For example, for administration to the shoulder or knee joints of an adult person (60 kg of body weight), a single dose of about 1 to about 10 ml, preferably about 2.5 ml of the preparation containing the erythropoietin antagonist at the concentration of about 100 to 4000 μg may be administered to the subject once to three times daily. A single dose of about 0.5 to about 5 ml, preferably about 1.5 ml of the preparation may be injected to the wrist joint, cubital joint and ankle once to three times daily. A single dose of about 0.5 to about 5 ml, preferably about 1 ml of the preparation may be injected to the flexor and extensor tendon sheath of arms and legs once to three times daily. A single dose of about 0.1 to about 1 ml of, preferably about 0.5 ml of the preparation may be injected to the interphalangeal articulations once to three times daily.

When the preparation of the present invention is a sustained release preparation, the dosage varies depending on the species and content of the erythropoietin antagonist, dosage form, duration of drug release, subject animal (mammals, for example, human beings, rats, mice, cats, dogs, rabbits, cattle, pigs, etc.) and purpose of administration. For example, in case of parental administration, the preparation may be administered so that about 0.1 to about 100 mg of the erythropoietin antagonist is released each week.

The preparation of the present invention may contain or be combined with medicinal component(s) other than the erythropoietin antagonist as the active component(s). Examples of the medicinal components include antiallergic agents (for example, ketotifen, terfenadine, azelastine, epinastine, etc.), antimicrobial agents (for example, cefixime, cefdinir, ofloxacin, tosufloxacin, etc.), antifungal agents (for example, fluconazole, itraconazole, etc.), anti-inflammatory steroids (for example, prednisolone, hydrocortisone, methylprednisolone, dexamethasone, betamethasone, etc.), non-steroidal anti-inflammatory agents (for example, indomethacin, diclofenac, loxoprofen, ibuprofen, aspirin, piroxicam, sulindac, cyclooxygenase inhibitors (for example, celecoxib, rofecoxib, etc.), etc.), disease-modifying antirheumatic agents and immunizing agents (for example, methotrexate, leflunomide, prograf, sulfasalazine, D-penicillamine, oral gold preparation, etc.), hyaluronate preparations (for example, sodium hyaluronate, etc.), and the like. There is no particular limitations on these components as long as the objectives of the present invention are achieved. They may be non-peptidic or peptidic, and can be used in an appropriate mixing ratio.

For combining the preparation of the present invention and a drug to be combined, there is no limitation on administration timing of the preparation of the present invention and the drug, and the preparation of the present invention and the drug may be administered to subjects simultaneously or separately with a time lag. The dosage of a drug to be combined may be that used in clinical practice, and is appropriately selected according to a particular subject, administration route, disease, combination, etc.

There is no particular limitation on dosage forms of the preparation of the present invention and a drug to be combined as long as the preparation of the present invention and the drug are combined when they are administered. For example, such dosage forms include (1) administration of a single preparation obtained by formulating the preparation of the present invention and a drug to be combined therein; (2) simultaneous administration of the preparation of the present invention and a. drug to be combined in the form of separately prepared two different preparations via the same administration route; (3) separate administration of the preparation of the present invention and a drug to be combined in the form of separately prepared two different preparations via the same administration route with a time lag; (4) simultaneous administration of the preparation of the present invention and a drug to be combined in the from of separately prepared two different preparations via different routes; (5) separate administration of the preparation of the present invention and a drug to be combined in the form of separately prepared two different preparations via different routes with a time lag (for example, administration of the preparation of the present invention followed by administration of a drug to be combined, or administrations in the reverse order). These dosage forms are collectively abbreviated to as "the combined preparation of the present invention" hereinafter.

The combined preparation of the present invention is less toxic and the preparation of the present invention and/or a drug to be combined are mixed with a pharmaceutically acceptable carrier according to a per se known method to obtain a pharmaceutical composition.

As the pharmaceutically acceptable carrier that can be used for the production of the combined preparation(s) of the present invention, there can be used the same as that used in the above-mentioned pharmaceutical composition of the present invention.

When the preparation of the present invention and a drug to be combined are simultaneously formulated and used as a single preparation, usually, the content of erythropoietin antagonist is about 0.1 to about 100% by weight, preferably about 10 to about 99.9% by weight, more preferably about 20 to about 90% by weight of the whole preparation, though this varies depending on a particular dosage form.

Further, although the content of a drug to be combined in the combined preparation of the present invention varies depending on a particular dosage form, usually, it is about 0.1 to about 100% by weight, preferably about 10 to about 99.9% by weight, more preferably about 20 to about 90% by weight of the whole preparation.

In the combined preparation of the present invention, although the contents of components other than the erythropoietin antagonist and a drug to be combined vary depending on a particular dosage form, usually, it is about 10 to about 99.9% by weight, more preferably about 20 to about 90% by weight of the whole preparation.

The mixing ratio between the erythropoietin antagonist and a drug to be combined in the combined preparation of the present invention may be appropriately selected depending on a particular subject, administration route, disease, etc.

The dosage of the combined preparation of the present invention varies depending on particular species of the erythropoietin antagonist and a drug to be combined, administration route, disease conditions, age of a patient, etc. However, for example, in case of topical application for the purpose of treating keloid, a single dose of about 0.1 to about 100 mg, preferably about 1 to about 50 mg, more preferably about 2 to about 20 mg in terms of the erythropoietin antagonist and the drug may be administered to an adult person (60 kg of body weight) once to three times daily.

The same contents may be employed in cases where the erythropoietin antagonist contained in the preparation of the present invention and a drug to be combined are separately formulated in different preparations, respectively.

When the erythropoietin antagonist contained in the preparation of the present invention and a drug to be combined are separately formulated and administered as different preparations, respectively, the preparation of the present invention and a pharmaceutical composition containing a drug to be combined may be simultaneously administered. Alternatively, the preparation of the present invention may be administered after a pharmaceutical composition containing a drug to be combined is administered, or the preparation of the present invention may be administered first and then a pharmaceutical composition containing a drug to be combined is administered. When separately administered with a time lag, the time lag varies depending on particular active components to be administered, dosage form and administration route. However, for example, when a pharmaceutical composition containing a drug to be combined is administered first, the preparation of the present invention may be administered within 1 minute to 3 days, preferably 10 minutes to 1 day, more preferably 15 minutes to 1 hour after the administration of the pharmaceutical composition containing the drug to be combined. When the preparation of the present invention is administered first, a pharmaceutical composition containing a drug to be combined may be administered within 1 minute to 1 day, preferably 10 minutes to 6 hours, more preferably 15 minutes to 1 hour after the administration of the preparation of the present invention.

EXAMPLES

The following Examples further illustrate the present invention in detail, but they are mere examples and are not to be construed to limit the scope of the present invention.

Example 1

Production of Anti-erythropoietin Antibodies (1) Preparation of Antigen EPO

According to the method described in JP 60-41614 A, EPO isolated from urine of patients with anemia (EPO sample obtained by SDS treatment of concentrated urine of patients with anemia followed by antibody adsorption treatment and gel filtration) was dissolved in PBS and this was ice-cooled. To this was added 9-fold volumes of 99.5% ethanol cooled at −20° C. to precipitate EPO. After washing with 90% ethanol solution cooled at −20° C., the precipitate was dried under reduced pressure, and then dissolved in 10 mM Napi buffer (pH 6.8) containing 0.01 mM $CaCl_2$. The solution was applied to a hydroxyapatite column equilibrated in advance with the same buffer, and EPO was recovered in a non-adsorbed fraction. The purity of the EPO thus obtained was 99%. This EPO was used for preparation of anti-EPO antibodies according to the method described JP 01-228492 A as follows.

(2) Immunization of an Experimental Animal with the Above EPO

The purified EPO prepared according to the above-mentioned method was used as an antigen, and a mouse (BALB/c mouse) was used as an experimental animal. The mouse was immunized three times at the intervals of two weeks as follows.

First Immunization:

The purified EPO was dissolved in PBS at a concentration of 1 mg/ml and mixed with an equal volume of Freund's complete adjuvant to obtain an emulsion. The mouse was challenged with 0.2 ml of the emulsion by intraperitoneal injection.

Second Immunization:

Two weeks later, 100 µl of the same emulsion was administered to the mouse by intraperitoneal injection.

Third Immunization:

Two weeks later, the purified EPO was dissolved in PBS at a concentration of 0.5 mg/ml, and 100 µl of the solution was administered to the mouse by intraperitoneal injection.

(3) Preparation of Anti-EPO Antibody Producer Hybridoma i) Preparation of Cell Fusion Spleen cells were aseptically removed from the immunized mouse three days after the completion of the above immunization and washed with a mixture of a synthetic medium (PRMI1640; Gibco BRL) and 15% fetal calf serum (FCS). The spleen cells were minced into single cells with a pair of scissors in the mixture and then washed twice with the same mixture. The isolated single cells were dispersed in PRMI1640 solution. The number of cells was $8 \times 10^8$. Separately, mouse myeloma cells (P3/NSI/1-Ag4-1) were cultured in the above mixture of PRMI and FCS, and the proliferated cells were washed with PRMI1640 solution. The number of cells was $4 \times 10^8$.

Then, the spleen cells from the immunized mouse and mouse myeloma cells prepared as described above were dispersed and mixed in PRMI1640 solution, followed by centrifugation to remove the supernatant. The mixed cells were subjected to cell fusion in a 50% polyethylene glycol 1500 solution. The fused cells were mixed with a HT culture solution (PRMI1640 solution containing hypoxanthine, thymidine and 15% fetal calf serum), and the mixture was seeded on eight 96-well microtiter plates. More than two days later, a HAT solution (PRMI1640 solution containing hypoxanthine, thymidine and 15% fetal calf serum) was added to the wells, and the cells were cultured for two weeks in each well and subjected to HAT selection. Proliferated hybridoma cells were confirmed.

ii) Selection by Screening of the Above Hybridoma Cells

To select specific cells, i.e. hybridomas that produce antibodies capable of specifically binding to EPO, from the hybridomas obtained above, $^{125}$I-EPO (purified EPO derived from human urine and labeled with $^{125}$I-EPO using IODO-GEN method; 98 µCi/µg EPO) was used. The presence of antibodies specifically binding to $^{125}$I-EPO in the hybridoma cultures was confirmed and the cells were selected.

As a result, 25 different cells suitable for the purpose were selected. Eight kinds of the cells that showed higher affinity for the $^{125}$I-EPO were subcultured and cloned by limiting dilution to isolate monoclones. Thus, five kinds of hybridoma cells that stably produce antibodies were obtained. Among the five kinds of hybridoma cells, one that had most favorable adsorption and elution of EPO activity (n-#2) was used for the production of a monoclonal anti-EPO antibody.

(4) Production of Monoclonal Anti-EPO Antibody

The hybridoma cells n-#2 were used to produce an antibody. Namely, according to the similar manner as that described above, an antibody was produced in the abdominal cavity of a mouse and subjected to fractionation with 50% ammonium sulfate, followed by applying to a column packed with DE52 (DEAE-cellulose; Whatman), thereby obtaining purified immunoglobulins (IgG) as a 0.1M to 0.2M NaCl fraction. Thirty mice were used to obtain 900 mg of a purified monoclonal antibody (R2).

Example 2

Production of Soluble Erythropoietin Receptor Protein

According to the method described in Example 3 of JP 06-38787 A, the sEPO-R expression vector, pcmEPR sol·dhfr, was constructed and this gene was transfected into E. coli MC1061/P3 (this bacterial strain has been deposited with Bikoken (presently National Institute of Bioscience and Human-Technology, Agency of Industrial Science and Technology) under the accession number 12814). In the present invention, the above plasmid was isolated from these E. coli cells and transfected into CHO·dhfr cells. The sEPO-R expression vector, pcmEPR sol·dhfr, was introduced into CHO(dhfr-) cells by calcium phosphate method, and cells producing soluble erythropoietin receptor protein (sEPO-R) were selected. The sEPO-R gene was amplified with methotrexate (MTX) to obtain sEPO-R high producer cell strain N14.2. The cell strain obtained was proliferated in a nucleic acid-free α-MEM synthetic medium supplemented with 10% dialyzed fetal calf serum and 100 nM MTX. Then, the medium was exchanged with OPTI-MEMI medium (Gibco) containing 0.5% dialyzed fetal calf serum to produce sEPO-R. To 200 ml of the culture obtained was added 6 ml of EPO-immobilized CH-Sepharose 4B (15 mg EPO/ml gel), and they were gently brought into contact with each other overnight at 4° C. overnight. Then, the immobilization support was washed with 10-fold volumes of PBS, and sEPO-R bound to the support was eluted with PBS containing 1.5 M $MgCl_2$. The eluate was concentrated by ultrafiltration and the solvent was replaced with PBS, followed by molecular sieving by HPLC using TSKgel G3000SW (Toso) to obtain partially purified sEPO-R (0.6 mg). The molecular weight of the sEPO-R thus obtained was determined using SDS-PAGE and Sephadex G-75 gel filtration, and was shown to be about 33 kDa.

Example 3

Production of Ointment

The anti-erythropoietin antibody obtained in Example 1 was mixed with vaseline to produce an ointment.

Example 4

Production of Injectable Preparation 1

The anti-erythropoietin antibody obtained in Example 1 was dissolved in physiological saline to prepare 1 g/ml or 10 g/ml solution. The solution was filtered, and 200 μl portions thereof were distributed into sterile micro-tubes, and freeze-stored to obtain an injectable preparation. Upon use, this is dissolved in physiological saline.

Example 5

Production of Injectable Preparation 2

The erythropoietin receptor protein obtained in Example 2 was dissolved in physiological saline to prepare 200 μg/ml solution. This was filtered, and 200 μl portions thereof were distributed into sterile micro-tubes, and freeze-stored to obtain an injectable preparation. Upon use, this is dissolved in physiological saline.

Example 6

Effect of Erythropoietin Antagonists (Anti-erythropoietin Antibody) on Keloid

1) Immunostaining

As tissue research materials, tissue samples were removed from 4 cases of patients with keloid and 2 cases of patients with hypertrophic scars, and the samples were fixed for 6 hours with a fixing solution (Zamboni; Zamboni L. and DeMartino C., J. Cell Biol., vol. 35, p. 148A (1967)). Then, they were placed in a 25% sucrose solution and stored in a cold and dark place. Pieces of these samples were embedded using OCT compound (Mile), frozen in liquid nitrogen, and cut with a cryostat to obtain frozen sections of 7 μm in thickness. The sections were reacted with primary antibodies, i.e., anti-erythropoietin antibody (Genzyme), anti-erythropoietin receptor antibody (Yasuda Y. et al., Develop. Growth Differ., vol. 35, pp.711-722 (1993)), anti-Factor VIII antibody (Dako), collagen III antibody (Chemicon) or anti-collagen I antibody (Chemicon), and with an secondary antibody biotinylated anti-rabbit antibody (Vector). Subsequently, the sections were subjected to DAB reaction using a ABC kit (Vector) to develop color, followed by microscopic examination.

2) Tissue Transplantation

Keloid tissues were transplanted to nude mice to confirm the inhibitory effect of the preparation of the present invention on proliferation of keloid. As transplantation materials, tissue pieces removed from patients with keloid were placed in a culture medium (MEM+10% FCS+PC+SM) and stored in a cold and dark place until transplantation. Then, a piece of keloid tissue was transplanted into each of five nude mice (Balb/c, Jcl-nu, Clear Japan Inc.) of 6-week old subcutaneously in the interscapular region under anesthesia. After the transplantation, sizes (major axis×minor axis×height) of tumors grown from the proliferated keloid tissue were measured with a micrometer caliper three times a week. In the third month, the tumor growth was stabilized, and 200 μl of a 400 U/ml or 800 U/ml erythropoietin solution was injected into the tumors of five mice three times at one hour intervals. Further three months later, 200 μl of a 8 mg/ml solution of anti-erythropoietin antibody (R2) obtained in Example 1 was injected into the tumors of two mice via the skin at one hour intervals. To two control mice, 200 μl of physiological saline or mouse whole serum was injected three times in the same manner. The remaining one mouse was received no injection. One week after the injection, tumors were excised from the R2-injected and serum-injected mice and fixed. Four weeks after the injection, tumors were excised from the remained R2-injected and serum-injected mice and fixed. The results are shown below.

Figure 1:
FIG. 1 is a photomicrograph showing many fibroblasts with positive reactivity to anti-erythropoietin receptor antibody in keloid sections removed from a patient.

1. Pathological Tissue Examination of Keloid Tissue a) Erythropoietin Expression in Keloid Tissue Many fibroblasts and capillary endothelial cells that produce collagen showed a positive reactivity to the anti-erythropoietin receptor antibody (FIG. 1). These observations have revealed that fibroblasts and capillary endothelial cells respond to erythropoietin.

b) Presence of Type III Collagen Fibers in Keloid Tissue

Figure 2:
FIG. 2 is a photomicrograph showing many fibroblasts with positive reactivity to anti-type III collagen antibody in keloid sections removed from a patient.

Fibroblasts showed a strong positive reactivity to the collagen III antibody (FIG. 2). Collagen fiber bundles are also positive but the reactivity is weak in comparison with fibroblasts present in their periphery (FIG. 2).

c) Vascular Distribution in Keloid Tissue

Figure 3:
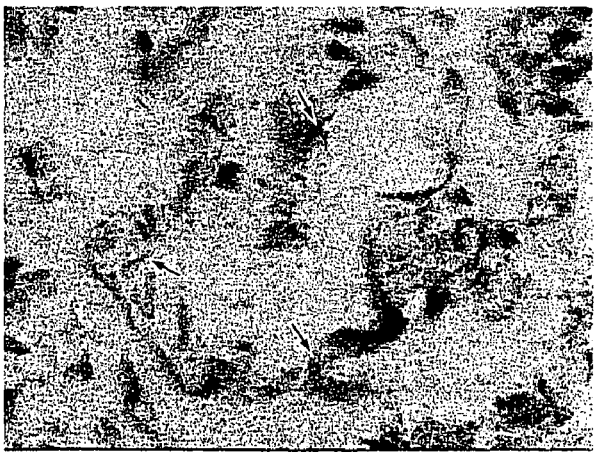
FIG. 3 is a photomicrograph showing distribution of many capillaries that exhibit a positive reactivity to anti-factor VIII antibody in keloid sections removed from a patient.

Many capillary endothelial and endothelial cells showed a positive reactivity to the anti-Factor VIII antibody which is an antibody to be used for identification of endothelial cells (FIG. 3).

2. Transplantation of Keloid Tissue a) Developments After Transplantation

Pieces of keloid tissue were transplanted subcutaneously. After the transplantation, local swellings (tumors) were observed. When the tumor growth was slowed down in comparison with that immediately after the transplantation (16 weeks later), a 400 U or 800 U of erythropoietin solution was topically injected three times at one hour intervals into each tumor, and the increase in the growth rate was observed (Table 1). Ten days after the administration, a tumor was removed from one case, but a tumor appeared 3 weeks later. R2 was injected topically three times at one hour intervals, 28 weeks after the transplantation. Tumors were excised 1 or 4 weeks later.

b) Growth of Transplanted Tumors by Administration of Erythropoietin

As shown in Table 1, in the two cases, the sizes of tumors were increased 6 to 9-fold and 8 to 7.5-fold, respectively, in comparison with those before the transplantation as of 12 and 24 hours after the erythropoietin administration. The sizes of tumors were still 3-fold even 4 days after the administration. No difference was observed between the concentrations of erythropoietin administered.

c) Suppression of Transplanted Tumors by Anti-Erythropoietin Antibody Administration Table 2 shows the changes in the sizes of tumors before and after administration of an anti-erythropoietin antibody. The antibody-administered mouse (No. 3) showed slight tumor suppression. Further, in mouse No. 4, softness of the tumor was diminished and the tumor was turned into a hard tumor-like swelling. The pathological examination of the proliferated tumor of mouse No. 3 and the remaining soft tissue of mouse No. 4 gave no clear pathological observation of keloid lesions as mentioned hereinafter, and instead, calcification of the tissue due to destruction of the transplanted tissue and calcium deposition were observed in three-fourths of the tumor-like swelling.

TABLE 1

| Nude mice transplantation number | Concentration U/ml (dose μl) | Frequency of administrations 1 hr intervals | Growth rate after administration* (Ratio) | | | |
|---|---|---|---|---|---|---|
| | | | 1 hr. | 12 hrs. | 24 hrs. | 4 days |
| 1 | 400 (200) | 3 | 1.4 | 1.1 | 1.1 | 1.1 |
| 2 | 400 (200) | 3 | 4.1 | 6.0 | 8.0 | 3.0 |
| 3 | 800 (200) | 3 | 2.0 | 9.3 | 7.5 | 3.2 |

*Volume of the tumor after the administration/Volume of the tumor at 16 weeks after the transplantation and prior to the administration

TABLE 2

| Nude mice number | Administered agent and its concentration (dose μl) | Frequency of administrations | Changes after administration* |
|---|---|---|---|
| 1 | Physiological saline (200) | 3 times | 0.63 (Week 4) |
| 2 | Mouse serum (200) | 3 times | 0.94 (Week 1) |
| 3 | 8 mg/ml, R2 (200) | 3 times | 0.61** (Week 4) |
| 4 | 8 mg/ml, R2 (200) | 3 times | 1.74*** (Week 1) |

* = Weight of the transplanted tumor one or four weeks after the administration/Weight of the transplanted tumor at 28 weeks after the administration
**A tumor-like swelling was soft and elastic.
***The softness and elasticity were diminished and a hard tumor-like swelling was recognized by palpation.

Figure 4:
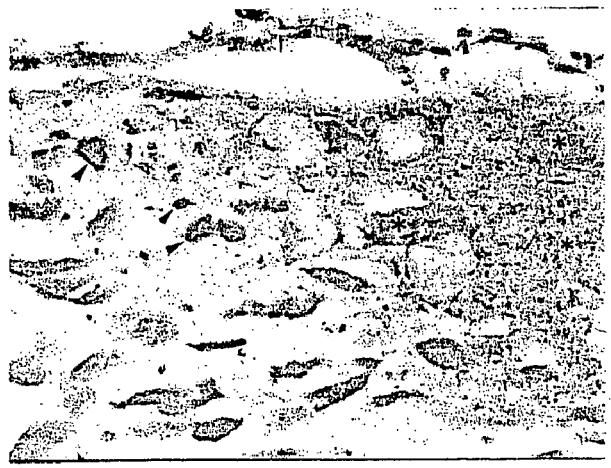
FIG. 4 is a photomicrograph showing calcified tissue of a tumor section obtained from a nude mouse transplanted a block of keloid tumor one week after injection of anti-erythropoietin antibody three times to the tumor continuously.
Figure 5:
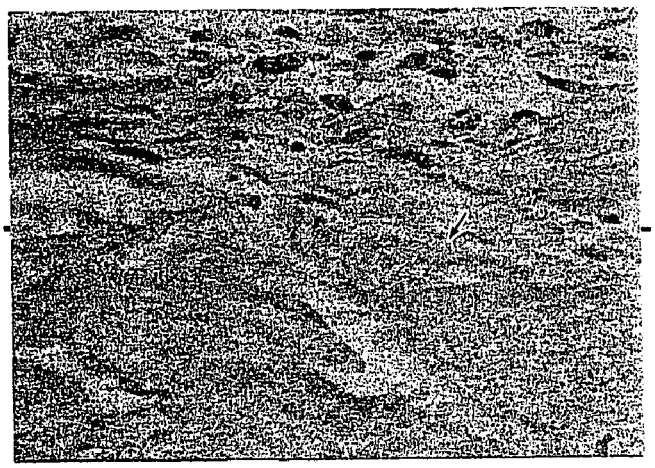
FIG. 5 is a photomicrograph showing the tumor tissue sections obtained from nude mice transplanted a block of keloid tumor one week after injection of mouse serum three times to the tumor continuously.
Figure 6:
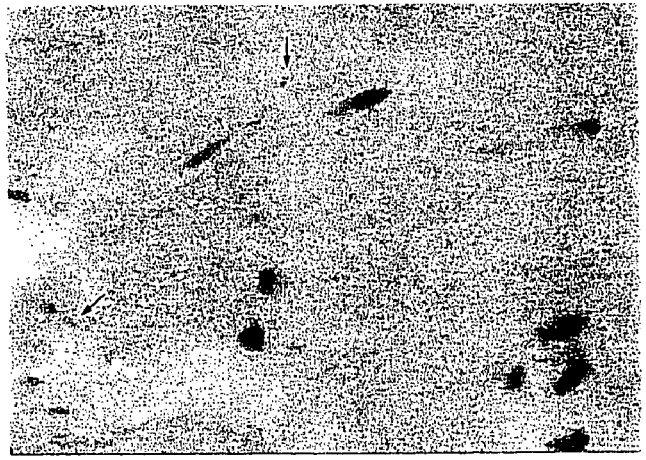
FIG. 6 is a photomicrograph showing a positive reactivity to the anti-factor VIII antibody in the same specimen as shown in FIG. 4 (treated with R2 three times).
Figure 7:
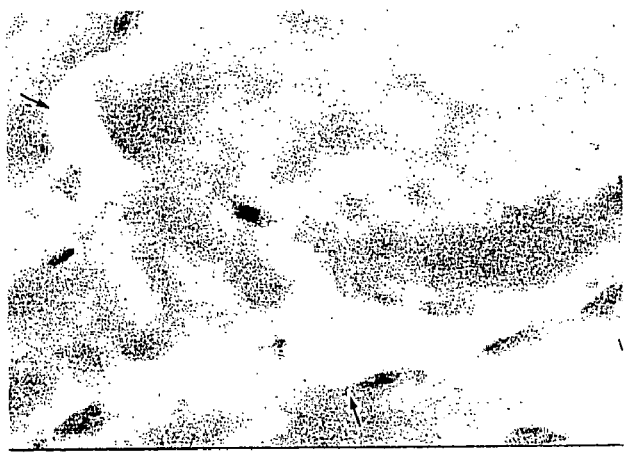
FIG. 7 is a photomicrograph showing a positive reactivity to the anti-factor VIII antibody of the same specimen as shown in FIG. 5 (treated with mouse serum three times).

Pathological Features a) Changes in transplanted tumor caused by injection of anti-erythropoietin antibody i) Remarkable disruption of the fiber bundles of type III collagen is observed in the R2 treatment. The disrupted bundles are attacked by leukocytes, macrophages and NK-like cells, and melted and disappeared to remain only fibers. Fibroblasts show chromatin condensation, and accumulation of dead cells are observed (FIG. 4).

ii) In the control treatment, the presence of proliferated collagen fiber bundles is recognized. Fibroblasts and fiber cells show no degeneration (FIG. 5).

b) The density of vascular vessels in the vicinity of collagen bundles is low in the transplanted tumors in comparison with that before the transplantation.

i) Death of the endothelial cells was observed in the R2-treated tumor (FIG. 6).

ii) The presence of the endothelial cells was observed in the control tumor (FIG. 7).

Figure 8:
FIG. 8 is a photomicrograph showing van Kossa-stained calcified tissue of the same specimen as shown in FIG. 4 (treated with R2 three times).

C) Calcium deposition in transplant pieces i) Calcium deposition was observed in all the R2 treatment. In mouse No. 4, three-fourths of the tumor showed calcification, collagen bundles in the vicinity of calcified tissue were disrupted, and disrupted collagen were calcified (FIG. 8).

ii) Calcium deposition was observed in one tumor in the saline-treated mice. However, no change of the collagen bundles in the vicinity of calcification was observed, and an proliferation image was shown.

These results are summarized in Table 3. Almost no changes were observed in the tissues of the untreated and control groups, while, in the anti-erythropoietin antibody-treated group, degeneration of fibroblasts, disruption and disappearance of collagen bundles, calcification of tissue due to calcium deposition, and suppression of collagen production were induced. These results have confirmed that the anti-erythropoietin antibody suppresses the keloid proliferation.

TABLE 3

| Mice Number | Treatment and time lag between treatment and removal | Fibroblasts | Type III collagen bundle | Endothelial cells | cell infiltration | calcium deposition |
|---|---|---|---|---|---|---|
| 4 | 8 mg/ml R2 1 week | Degeneration and necrosis/fragmented nucleus | disruption/ dissolution/ disappearance | many degenerated and necrotic | frequent | present, extensive calcification (almost all over the tissue) |
| 3 | 8 mg/ml R2 4 weeks | Degeneration and necrosis/fragmented nucleus | disruption/ dissolution/ disappearance | many degenerated and necrotic | frequent | present, focal calcification of the tissue |
| 2 | mouse serum 1 week | none | none | many necrotic | almost none | none |
| 1 | Physiological saline 4 weeks | none | none | frequent necrotic | almost none | Present, smaller than 4 and 3 |
| 5 | no treatment | none | none | none | none | absent |

Example 7

Effect of Erythropoietin Antagonists (Erythropoietin Receptor Protein) on Keloid According to the same manners as those described in Example 6, the experiment was carried out except that the erythropoietin receptor protein obtained in Example 2 was used instead of the anti-erythropoietin antibody. Like the results obtained using the antibody, it has been confirmed that the erythropoietin receptor protein suppresses keloid proliferation.

Example 8

Effect of Erythropoietin Antagonists (Anti-erythropoietin Antibody) on Rheumatoid Arthritis 1) Immunostaining As tissue research material, fragments of proliferating synovial membrane resected from five patients with rheumatoid arthritis by surgery were cut into small pieces of 20 mm×10 mm×5 mm, were fixed for six hours with a fixative (Zamboni; Zamboni L. and DeMartino C., J. Cell Biol., vol. 35, p. 148A (1967)), and stored in a cold and dark place after the solution was replaced with PBS containing 25% sucrose solution.

These sample pieces were embedded in OCT compound (Mile), frozen in liquid nitrogen, and cut with a cryostat to obtain frozen sections of 7 μm in thickness. The sections were reacted with any one of the five primary antibodies, namely i) anti-erythropoietin receptor antibody (Yasuda Y. et al., Develop. Growth Differ., vol. 35, pp.711-722 (1993)), ii) anti-IL-1α antibody (Genzyme), iii) anti-collagen III antibody (Chemico) iv) anti-estrogen receptor antibody (Chemico) and v) anti-Factor VIII antibody. Subsequently, the samples, which had been reacted with i), iii) or v), were reacted with the secondary antibody, biotinylated anti-rabbit antibody (Vector), and the samples, which had been reacted with ii) or iv), were reacted with biotinylated anti-mouse-antibody (Chemico). Then, the sections were subjected to DAB reaction (Dojin Pharmaceutical or WAKO Pure Chemical Industries, Ltd.) for coloring, followed by microscopic examinations.

2) Organ Culture

As materials for organ culture, samples resected from three cases among the above-mentioned cases were placed into a culture medium (MEM+10% FCS, 100 U/ml PC and 100 μg/ml SM) immediately after the surgery and washed. After washing, the samples were stored in the same solution in a cold and dark place until the culture started.

The fresh synovial membrane pieces thus prepared (within 10 to 24 hours after the surgery) were cut into small pieces of 2×5×10 mm and 50 to 100 mg by weight. One piece of the tissue was place in a 60 mm petri dish (3042; Falcon) and weighed. To the dish, a physiological saline solution containing the anti-erythropoietin antibody (R2) obtained in Example 1 at a concentration of 16 mg/ml and colored with addition of 0.25% Evans Blue was added. As a control, a physiological saline to which 0.25% Evans Blue was added (Otsuka Pharmaceuticals) was used. Injection was carried out with Hamilton gauge 32 needles (90131) and syringes (725). Into several sites of the tissue pieces, 0.5 μl per 1 mg of tissue, or 0.5 μl/mg tissue of R2 or physiological saline was injected. After the injection, the dish was covered and the reaction was carried out in the dish at 37° C. for 60 minutes under 5% $CO_2$ and 95% air. This procedure was repeated to treat with R2 or physiological saline three to four times, followed by organ culture of the tissue pieces in MEM+10% FCS medium in a 24-well culture plate (3047; Falcon) at 37° C. for 6 to 8 hours under 5% $CO_2$ and 95% air. There is a time lag between the culture periods because the culture period is expired 12 hours after the beginning of R2 treatment.

The cultured pieces were fixed in Zamboni's solution. Six hours later, the solution was replaced with PBS containing 25% sucrose solution and the pieces were stored in a cold and dark place, followed by subjecting to the pathological examination of the tissue. The results of the examination are shown below.

Characterization of Synovial Membrane Tissue of Rheumatoid Arthritis

1) Reaction Sites to Erythropoietin in Synovial Villi

Figure 9:
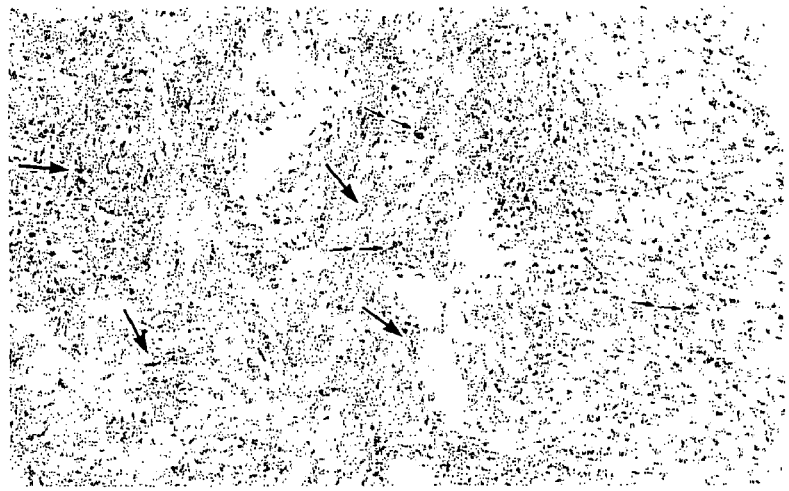
FIG. 9 is a photomicrograph showing cells reacted with anti-erythropoietin receptor antibody (arrows) and cell infiltration in synovial villous fragments resected from patient A.
Figure 10:
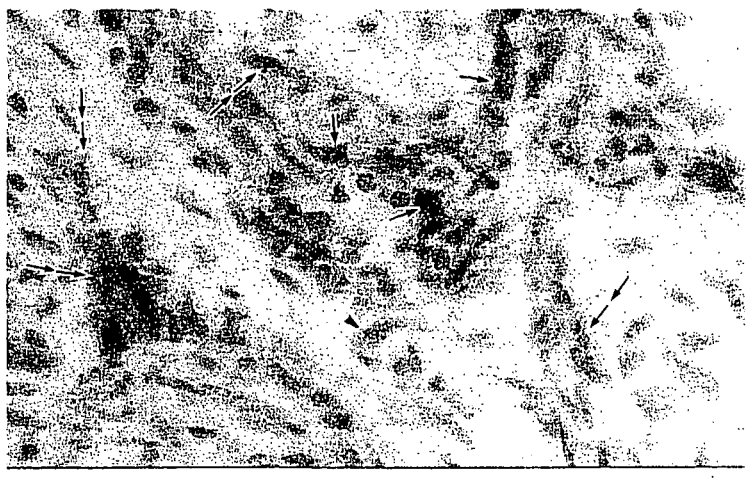
FIG. 10 is a photomicrograph showing a high power view of the portion of a synovial villous fragment resected from patient B that shows positive immunoreactivity to anti-erythropoietin receptor antibody.
Figure 11:
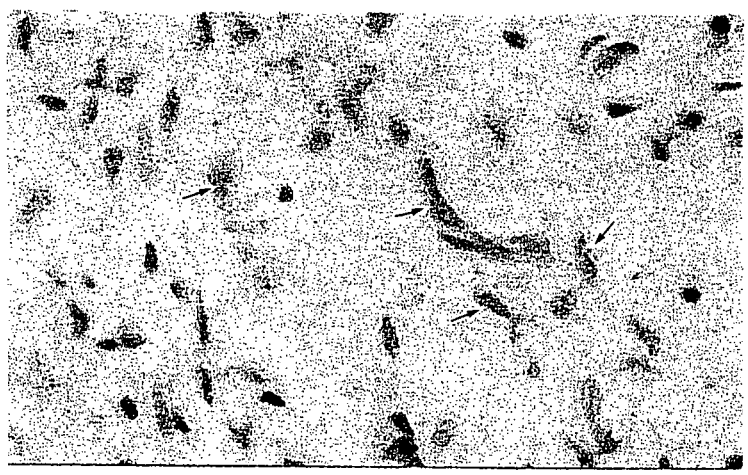
FIG. 11 is a photomicrograph showing fibroblasts that exhibit a positive reactivity to anti-erythropoietin receptor antibody in a tissue section resected from the same patient as shown in FIG. 10.

Collagen-producing fibroblasts, macrophages infiltrating the fiber bundles and synovial villi, monocytes, and capillary endothelial cells are the reaction sites to erythropoietin (FIGS. 9, 10 and 11).

2) IL-1α Expression in Synovial Villi

Figure 12:
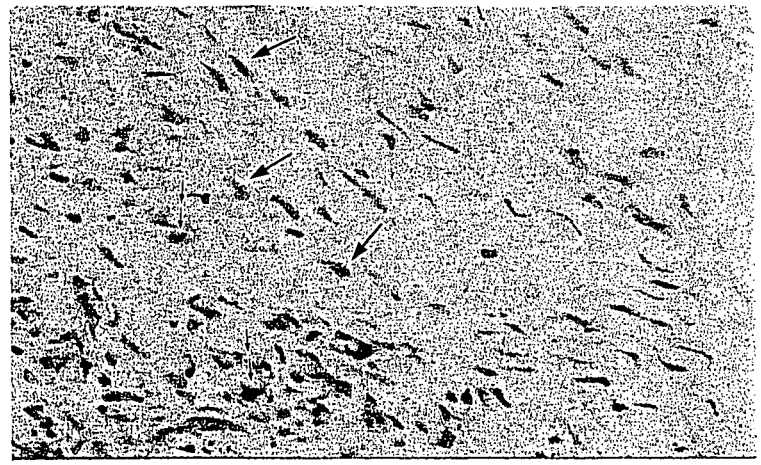
FIG. 12 is a photomicrograph showing fibroblasts and infiltrating cells that exhibit the positive reactivity to the anti-IL-1α antibody in tissue sections resected from the same patient as shown in FIG. 10.

The expression is recognized in collagen-producing fibroblasts, infiltrating monocytes, macrophage and lymphocytes (FIG. 12).

3) Vascular Distribution in Synovial Villi

Figure 13:
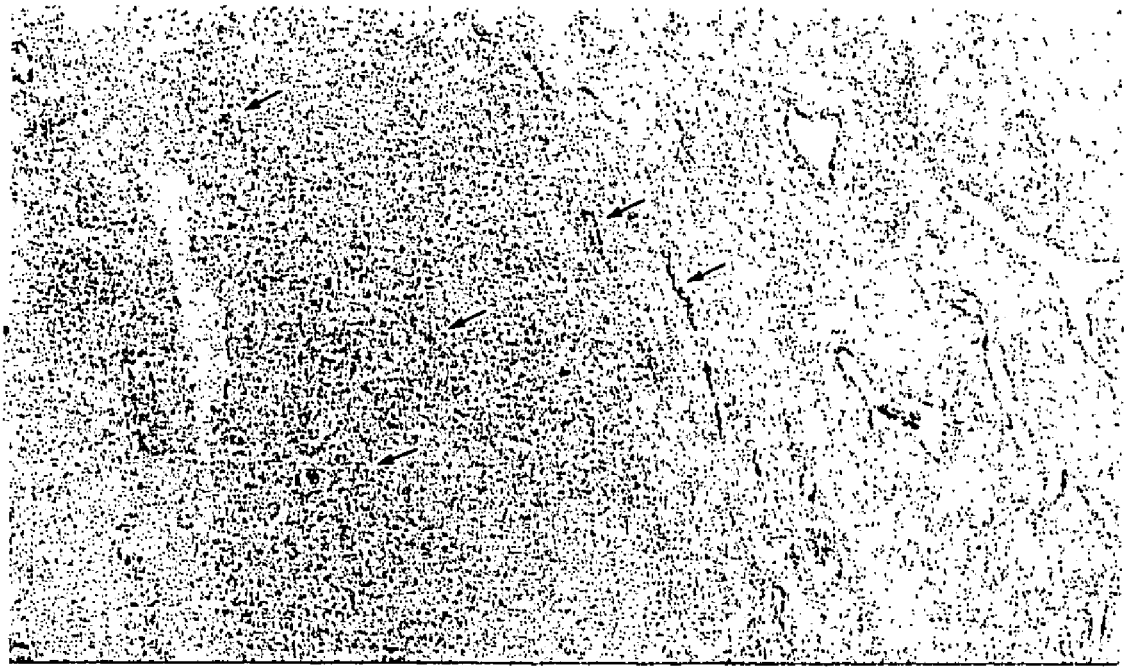
FIG. 13 is a photomicrograph showing capillaries reacting to anti-factor VIII antibody in tissue sections resected from the same patient as in FIG. 9.

There are many blood vessels of capillaries, arterioles and venules in the synovial villi, and many monocytes and lymphocytes are infiltrating in the perivascular space (FIG. 13).

4) Collagen in Synovial Villi

Figure 14:
FIG. 14 is a photomicrograph showing fibroblasts that show a positive reactivity to the collagen III antibody in tissue sections resected from the same patient as shown in FIG. 10.

Collagen in the villi is abundant in fibers mainly composed of type III collagen. Fibroblasts have nuclei containing oval-shaped reticular chromatins and the cytoplasm having type III collagen (FIG. 14).

5) Expression of Estrogen Receptor in Synovial Villi

Figure 15:
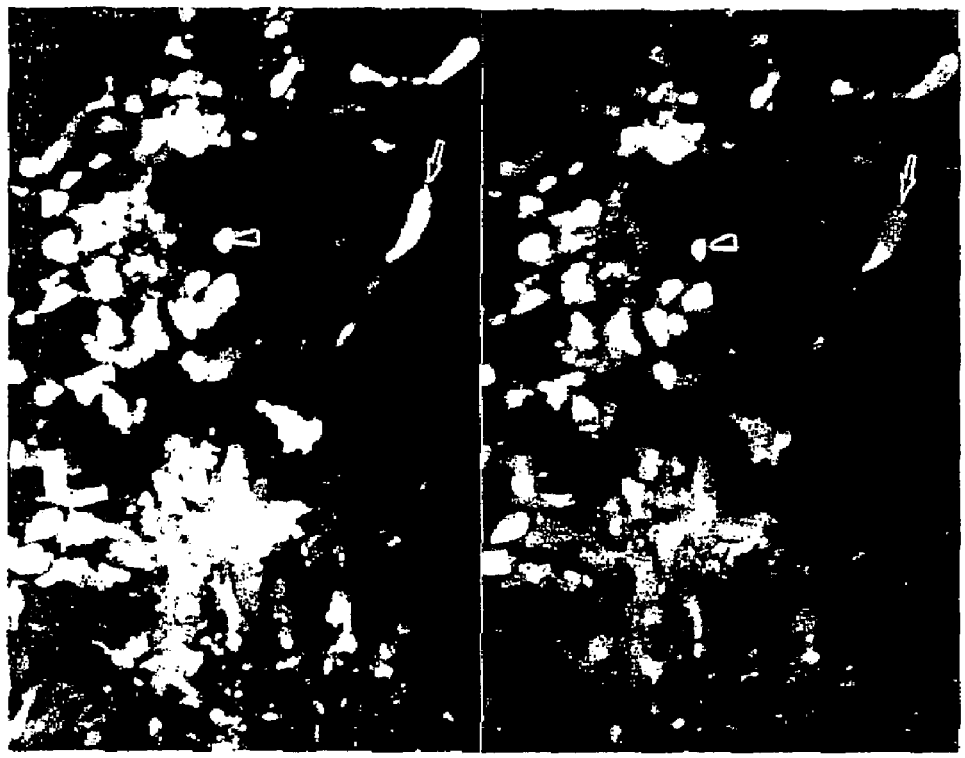
FIG. 15 is photomicrographs showing double staining of the same section with anti-erythropoietin receptor antibody (left panel) and estrogen receptor α antibody (right panel) resected from the same patient as shown in FIG. 10.
Figure 16:
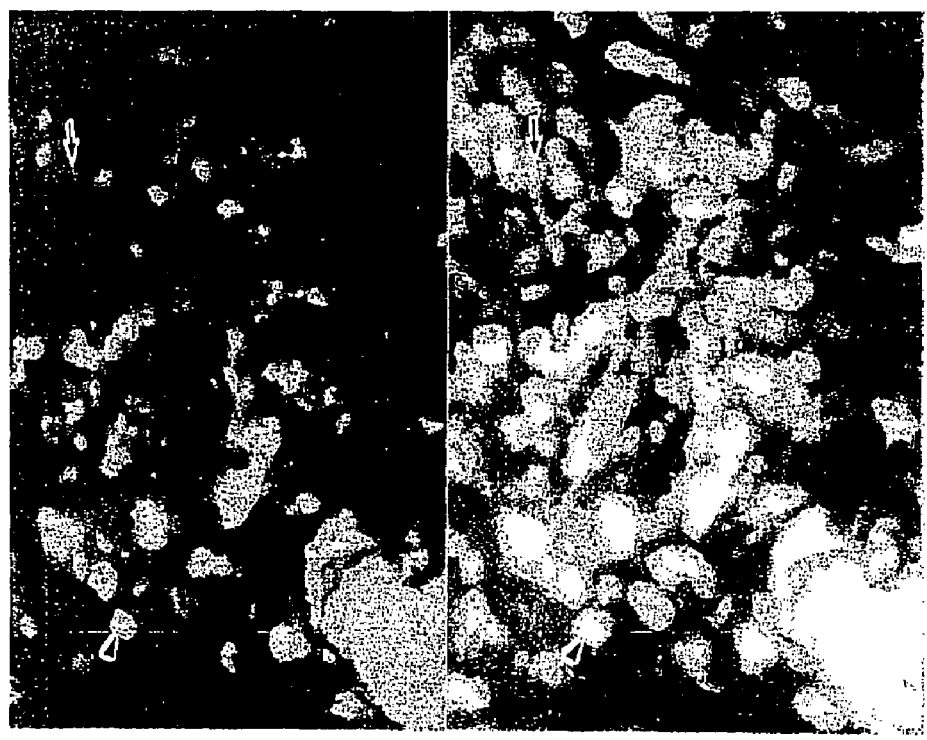
FIG. 16 is photomicrographs showing double staining of the same section with anti-erythropoietin receptor antibody (left panel) and the anti-ILα antibody (right panel) resected from the same patient as shown in FIG. 10.

In the villi, estrogen reaction sites (FIG. 15, right) correspond to the erythropoietin receptor (FIGS. 15, and 16, left) and the positive site to IL-1α (FIG. 16, right), and these three sites are coexisting with one another (FIGS. 15 and 16).

Changes in Synovial Villi by R2 Treatment

1) Death of Fibroblasts

Figure 17:
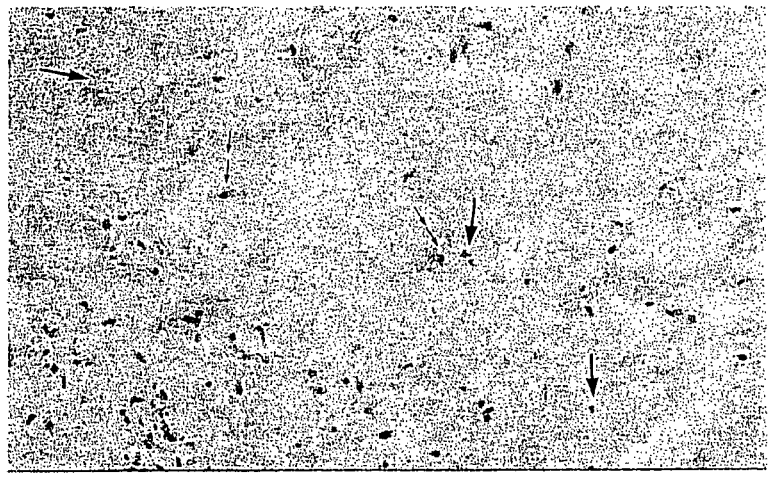
FIG. 17 is a photomicrograph showing a region which is positive to the collagen III antibody in tissue sections resected from the same patient as shown in FIG. 9, treated with R2 three times at one hour intervals and fixed 12 hours after beginning of the treatment.
Figure 18:
FIG. 18 is a photomicrograph showing a region which is positive to the collagen III antibody in tissue sections resected from the same patient as shown in FIG. 10, treated with R2 four times at one hour intervals and fixed 12 hours after beginning of the treatment.
Figure 19:
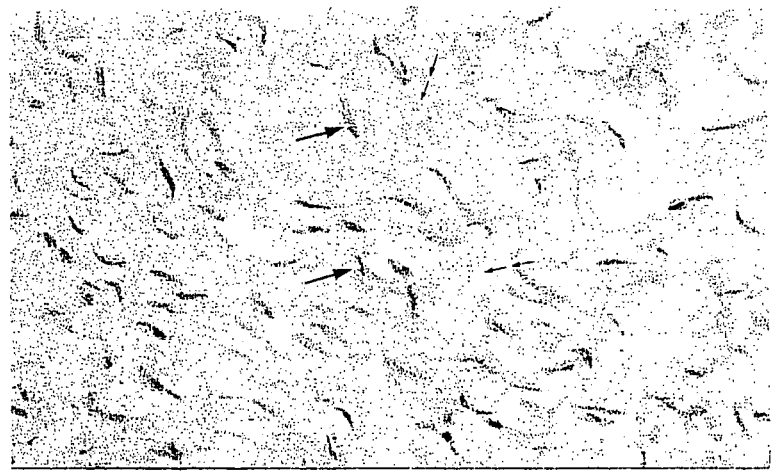
FIG. 19 is a photomicrograph showing a region which is positive to the collagen III antibody in tissue sections resected from the same patient as shown in FIG. 10, treated with physiological saline four times at one hour intervals and fixed 12 hours after beginning of the treatment.

Many dead fibroblasts were observed in three times (FIG. 17) and four times treatment (FIG. 18) with R2. Reticular chromatins were condensed and/or concentrated in the nuclei, and the cytoplasm was disappeared. This phenomenon is more prominent in four times treatment with R2 than three times, and is considered to be the death due to apoptosis. In the control group, no change in the fibroblasts was observed (FIG. 19).

2) Death of Monocytes, Lymphocytes and Macrophages

Figure 20:
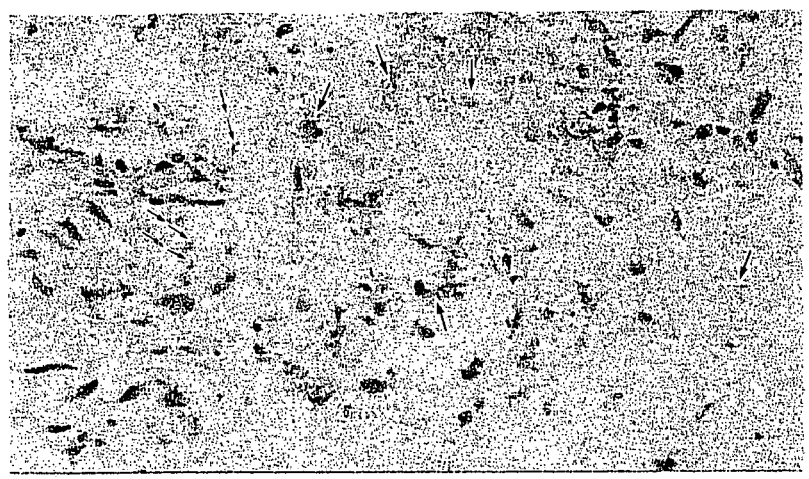
FIG. 20 is a photomicrograph showing a region which is positive to anti-IL-1α antibody in the sections of the same cultured block as shown in FIG. 18 (treated with R2 four times).
Figure 21:
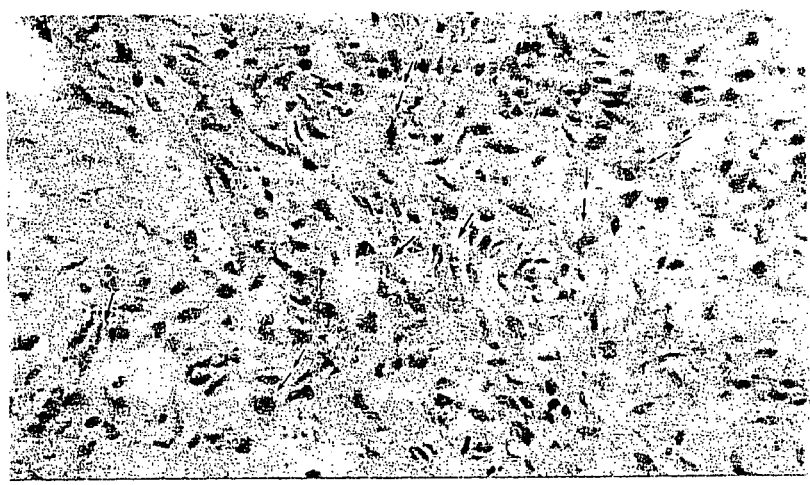
FIG. 21 is a photomicrograph showing a region which is positive to anti-IL-1α antibody in the sections of the same cultured block as shown in FIG. 19 (treated with physiological saline four times).

Dead lymphocytes, monocytes and macrophages with nuclear condensation were recognized in the perivascular region where cellular infiltration was frequently observed (FIG. 20). This phenomenon was more prominent in the treatment four times with R2 (FIG. 20), and the decrease in IL-1α-positive cells were observed in the cultured pieces. In the pieces of the control group, no change in infiltrated cells was observed (FIG. 21).

3) Disruption of Capillaries

Figure 22:
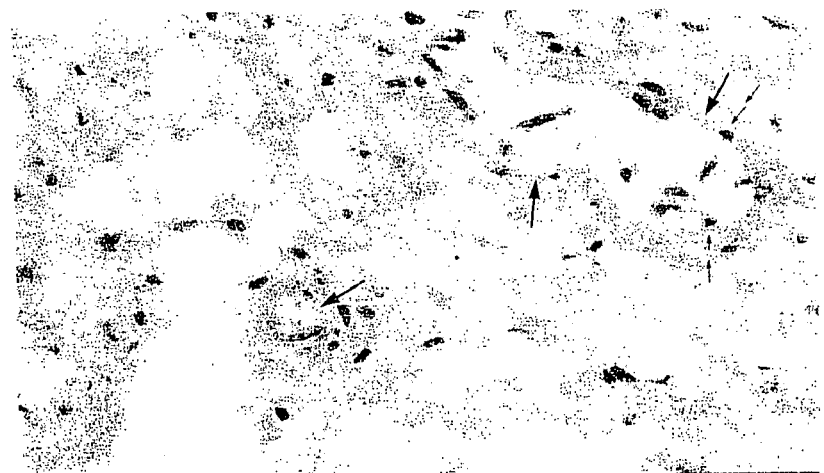
FIG. 22 is a photomicrograph showing a region which is positive to factor VIII in the sections of the same cultured block as shown in FIG. 17 (treated with R2 three times).
Figure 23:
FIG. 23 is a photomicrograph showing a region which is positive to factor VIII in the sections of the same cultured block as shown in FIG. 19 (treated with physiological saline four times).

Disappearance of blood capillaries was observed both in three times and four times treatment with R2 (FIG. 22). In the control group, there were many blood capillaries (FIG. 23).

4) Changes in Collagen Fibers

Disruption and decrease of collagen bundles were observed in three times (FIG. 17) and four times treatment (FIG. 18) with R2. In the control tissue pieces, no disruption and decrease of collagen bundles were observed (FIG. 19).

The above results are summarized in Table 4. The anti-erythropoietin antibody induced suppression of collagen production (degeneration and necrosis of fibroblasts and disappearance of collagen bundles) disappearance of blood capillaries, and necrosis of IL-1 secreting cells (necrosis of monocytes and macrophages) associated with the major condition of rheumatoid arthritis and the like, i.e. proliferation of synovial membrane. In view of these results, it has been confirmed that an anti-erythropoietin antibody can suppress inflammatory conditions of rheumatoid arthritis.

Example 9

Effect of Erythropoietin Antagonists (Erythropoietin Receptor Protein) on Rheumatoid Arthritis According to the same manners as those described in Example 8, the experiment was carried out except that a erythropoietin receptor protein was used instead of the anti-erythropoietin antibody. As a result, it has been confirmed that, like the results of the experiment obtained by using the antibody, the erythropoietin receptor protein also suppresses inflammation.

Example 10

Figure 24:
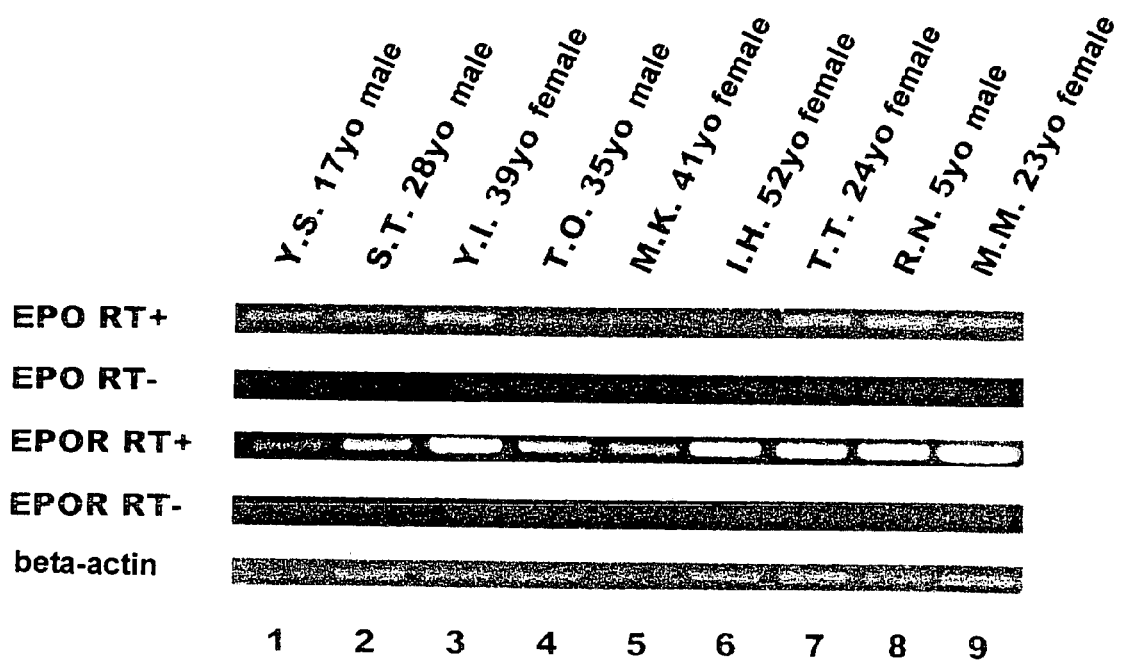
FIG. 24 is a photograph of the electrophoresis showing bands for erythropoietin mRNA and erythropoietin receptor mRNA in keloid tissue samples.

Expression of Erythropoietin and Erythropoietin Receptor mRNAs in Keloid Tissue Samples RNA's were extracted from the tissues of five cases of keloid scars, one case of an atrophic scar and three cases of red scars. Detection of the erythropoietin and erythropoietin receptor mRNA by RT-PCR was attempted using the RNA thus obtained. Expression of erythropoietin receptor mRNA was observed in all the cases. Expression of erythropoietin mRNA was high in the keloid scars and red scars, but very weak or nothing in the atrophic scar (FIG. 24). The conditions of the collected RNA's are considered to be fine since amplification of beta-actin mRNA is not weak.

Example 11

Expression of Erythropoietin and Erythropoietin Receptor mRNA in Synovial Membrane Tissue RNA's were extracted from the synovial membranes from eight patients, and detection of each mRNA was attempted by RT-PCR. Expression of mRNA for both erythropoietin and erythropoietin receptor was observed in all the cases, though the intension of each expression varied (FIG. 25).

Example 12

Erythropoietin Levels in Synovial Fluid

Synovial fluids obtained from nine patients with rheumatoid and five patients with osteoarthritis were used to determine the total protein content (mg/ml) and erythropoietin level (mU/ml). In both cases, although no difference between the protein contents was found, but the erythropoietin level in the rheumatic cases was significantly higher than that in the osteoarthritis cases.

The results are shown in Table 5

TABLE 5

|  | Erythropoietin level (mU/ml) mean ± standard error | Protein content (mg/ml) mean ± standard error |
|---|---|---|
| Rheumatoid n = 9 | 32.23 ± 7.16* | 28.82 ± 1.89 |
| Osteoarthritis n = 5 | 10.02 ± 0.79 | 22.30 ± 2.34 |

*$p < 0.05$

INDUSTRIAL APPLICABILITY

As is seen from the above description, according to

TABLE 4

| Treatment and frequency of treatment (Number of tissue pieces treated) | Pathological features | | | | |
| --- | --- | --- | --- | --- | --- |
| | Fibroblasts | Collagen III bundles | Vascular endothelial cells and capillaries | Monocytes | Macrophag s |
| 16 mg/ml R2 3 times (4) | Degeneration and Necrosis(+)* | Decrease (+) Disappearance(+) | Degeneration and Necrosis(+) | Death (+) | Death (+) |
| Physiological saline, 3 times (4) | No change** | No change | No change | No change | No change |
| 16 mg/ml R2, 4 times (5) | Degeneration and Necrosis(++) | Disruption (++) Decrease (++) Disappearance(++) | Degeneration and Necrosis(++) | Death (++) | Death (++) |
| Physiological saline, 4 times (5) | No change | No change | No change | No change | No change |
| no treatment (5) | positive to anti-IL-1 α antibody positive to anti-EpoR antibody positive to anti-Est-R α antibody (coexistence among three) | Proliferation | Present and many | Present and many in vessels | Frequent infiltration |

*Number of + represents the intensity
**No remarkable degeneration or necrosis as seen in the R2 treated group were observed.

the present invention, there is provided a pharmaceutical preparation which has excellent prophylactic and/or therapeutic effects on collagenous hyperproliferation such as hypertrophic scars, keloid, etc., or chronic arthritic diseases such as rheumatoid arthritis, etc.

The invention claimed is:

1. A method for treating hypertrophic scars or keloid in mammals which comprises administering an effective amount of an erythropoietin antagonist selected from the group consisting of an anti-erythropoietin antibody, an erythropoietin receptor protein and a soluble erythropoietin receptor protein to a mammal in need of such treatment.

2. The method according to claim 1, wherein the erythropoietin antagonist is an anti-erythropoietin antibody.

3. The method according to claim 1, wherein the erythropoietin antagonist is an erythropoietin receptor protein.

4. The method according to claim 3, wherein the erythropoietin receptor protein is a soluble erythropoietin receptor protein.

* * * * *